US008481779B2

(12) United States Patent
Ando et al.

(10) Patent No.: US 8,481,779 B2
(45) Date of Patent: Jul. 9, 2013

(54) METHOD FOR PRODUCING N-SUBSTITUTED-2-AMINO-4-(HYDROXY-METHYLPHOSPHINYL)-2-BUTENOIC ACID

(75) Inventors: Takashi Ando, Kanagawa (JP); Nobuto Minowa, Kanagawa (JP); Masaaki Mitomi, Kanagawa (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 0 days.

(21) Appl. No.: 13/579,135

(22) PCT Filed: Jun. 14, 2011

(86) PCT No.: PCT/JP2011/063546
§ 371 (c)(1),
(2), (4) Date: Aug. 15, 2012

(87) PCT Pub. No.: WO2011/158813
PCT Pub. Date: Dec. 21, 2011

(65) Prior Publication Data
US 2012/0316358 A1      Dec. 13, 2012

(30) Foreign Application Priority Data
Jun. 15, 2010   (JP) .................. 2010-136373

(51) Int. Cl.
C07F 9/30       (2006.01)
(52) U.S. Cl.
CPC .................................... C07F 9/302 (2013.01)
USPC ......................................................... 562/19
(58) Field of Classification Search
CPC .................................................... C07F 9/301
See application file for complete search history.

(56) References Cited

U.S. PATENT DOCUMENTS

| 4,399,287 | A | 8/1983 | Baillie et al. |
| 4,922,006 | A | 5/1990 | Zeiss |
| 7,795,464 | B2 | 9/2010 | Minowa et al. |
| 8,017,797 | B2 | 9/2011 | Minowa et al. |
| 2009/0221851 | A1 | 9/2009 | Minowa et al. |
| 2011/0009662 | A1 | 1/2011 | Kurihara et al. |

FOREIGN PATENT DOCUMENTS

| JP | 56-92897 | 7/1981 |
| JP | 62-226993 | 10/1987 |
| JP | 2-184692 A | 7/1990 |
| WO | 2008/029754 | 3/2008 |
| WO | 2008/114808 | 9/2008 |

OTHER PUBLICATIONS

Zeiss, Journal of Organic Chemistry, Enantioselective Synthesis of Both Isomers of Phosphinothricin via Asymmetric Hydrogenation of alpha-Acrylamido Acrylates, 1991, 58, pp. 1783-1788.*
Zeiss, "Enantioselective Synthesis of Both Enantiomers of Phosphinothricin via Asymmetric Hydrogenation of α-Acylamido Acrylates" J. Org. Chem. 56:1783-88, 1991.
Melillo et al., "Practical Enantioselective Synthesis of Homotyrosine Derivative and (R,R)-4-Propyl-9-hydroxynaphthoxazine, a Potent Dopamine Agonist" J. Org. Chem. 52:5143-50, 1987.
International Search Report for PCT/JP2011/063546 dated Sep. 20, 2011.
English Translation of International Preliminary Report on Patentability for International Application No. PCT/JP2011/063546, mailed Jan. 17, 2013.

* cited by examiner

Primary Examiner — Paul A Zucker
(74) Attorney, Agent, or Firm — Greenblum & Bernstein, P.L.C.

(57) ABSTRACT

Provided is a method for producing a compound expressed by the following formula (3):

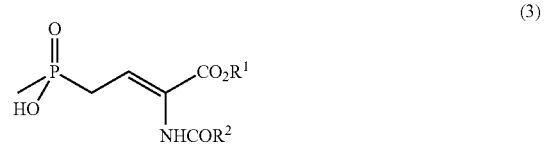

[where $R^1$ represents a hydrogen atom or $C_{1-4}$ alkyl group, and $R^2$ represents $C_{1-4}$ alkyl group, $C_{1-4}$ alkoxy group, aryl group, aryloxy group or benzyloxy group], the method comprising a reaction of dehydro-condensing a compound expressed by the following formula (1) and a compound expressed by the following formula (2):

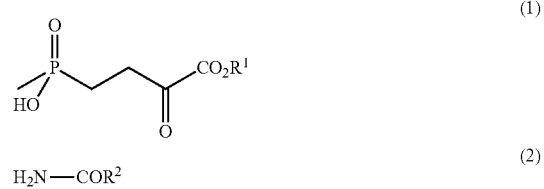

while being converted to a desired geometric isomer in the presence or absence of an acid catalyst, under a condition that an organic solvent to be used for the reaction is a mixed solvent of acetic acid and a solvent selected from the group consisting of toluene, xylene and chlorobenzene.

7 Claims, No Drawings

METHOD FOR PRODUCING N-SUBSTITUTED-2-AMINO-4-(HYDROXY-METHYLPHOSPHINYL)-2-BUTENOIC ACID

REFERENCE TO RELATED APPLICATION

This application is based upon and claims the benefit of the priority of Japanese patent application No. 2010-136373 (filed on Jun. 15, 2010), the disclosure thereof being incorporated herein in its entirety by reference thereto.

TECHNICAL FIELD

The present invention relates to a production of N-substituted 2-amino-4-(hydroxymethylphosphinyl)-2-butenoic acid derivative which is a useful production intermediate of herbicide, L-2-amino-4-(hydroxymethylphosphinyl)-butanoic acid (abbreviated as "L-AMPB" hereinafter).

BACKGROUND

It has been hitherto known that N-substituted 2-amino-4-(hydroxymethylphosphinyl)-2-butenoic acid derivative is a synthetic intermediate of L-AMPB having herbicidal activity (Japanese Patent Laid-Open No. 92897/1981 (Patent Document 1), J. Org. Chem., 56, 1783-1788 (1991) (Non Patent Document 1)).

Up to date, a method for synthesizing by condensing 2-oxo-4-(hydroxymethylphosphinyl)-2-butanoic acid and acetamide (Japanese Patent Laid-Open No. 226993/1987 (Patent Document 2)) and a method for synthesizing by condensing phosphinylacetaldehyde derivative and isocyanoacetate (Non Patent Document 1) have been reported as a method for producing N-substituted-2-amino-4-(hydroxymethylphosphinyl)-2-butenoic acid derivative.
Also, a method for synthesizing a phosphorylglycine derivative and a phosphinylacetaldehyde derivative by a reaction of Horner-Emmons type has been reported (Patent Document 3).

[Patent Document 1] Japanese Patent Laid-Open No. 92897/1981
[Patent Document 2] Japanese Patent Laid-Open No. 226993/1987
[Patent Document 3] WO 2008/114808
[Non-Patent Document 1] J. Org. Chem., 56, 1783-1788 (1991)

SUMMARY

The following analysis is provided by the present invention. The entire disclosures in each of the Patent Documents 1, 2, 3 and Non Patent Document 1 are incorporated and described herein by reference thereto.

However, the method of condensing 2-oxo-4-(hydroxymethylphosphinyl)-butanoic acid and acetamide described in Patent Document 1 is difficult to conduct in large amounts since a substrate needs to be heated with no solvent under a reduced pressure. On the other hand, methods for condensation with acetamide described in Patent Document 2 and Non Patent Document 1 result in a moderate yield, while solubility or dispersibility of substrate and reaction product in solvent are poor. In a result, there are problems of handling and reduction in yield associated with scale up. Further, as described in WO 2008/029754, a geometric isomer which is especially useful as a synthetic intermediate of L-AMPB is (Z)—N-substituted-2-amino-4-(hydroxymethylphosphinyl)-2-butenoic acid derivative (abbreviated as "Z form" hereinafter), however, there is no description of the correlation between reaction conditions and the synthetic ratio of Z form in Patent Document 2 and Non Patent Document 1.

On the other hand, a reaction substrate in the synthetic method by Horner-Emmons type reaction described in Patent Document 3 is different from that in the method of the present invention using 2-oxo-4-(hydroxymethylphosphinyl)-butanoic acid as a starting material. A method for condensing phosphinylacetaldehyde derivative and isocyanoacetate, described in Non Patent Document 1 is also different in the same point, in addition, there are problems of expensive reagents and difficulty in the preparation method of phosphinylacetaldehyde derivative. Thus, it has been desired to develop a production method in which industrial production can be achieved.

It is an object of the present invention to provide a method for producing (Z)—N-substituted-2-amino-4-(hydroxymethylphosphinyl)-2-butenoic acid derivative which is a production intermediate of L-AMPB that is useful as a herbicide, efficiently.

The present inventors scrutinized reaction conditions for dehydro-condensing 2-oxo-4-(hydroxymethylphosphinyl)-butanoic acid derivative and amide compounds described in Patent Document 2 and Non Patent Document 1, and as a result they found that N-substituted-2-amino-4-(hydroxymethylphosphinyl)-2-butenoic acid derivative can be obtained in a high yield greater than that in prior reports and thus completed the present invention.

That is to say, the present invention provides a method for producing a compound expressed by the following formula (3):

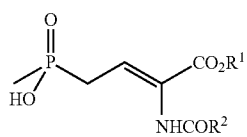

(3)

[where $R^1$ represents a hydrogen atom or $C_{1-4}$ alkyl group, and $R^2$ represents $C_{1-4}$ alkyl group, $C_{1-4}$ alkoxy group, aryl group, aryloxy group or benzyloxy group], the method comprising a reaction of dehydro-condensing a compound expressed by the following formula (1):

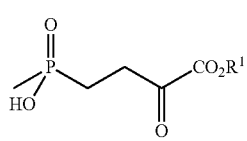

(1)

[where $R^1$ represents the same meaning as defined above], and a compound expressed by the following formula (2):

(2)

[where $R^2$ represents the same meaning as defined above], while being converted to a desired geometric isomer in the presence or absence of an acid catalyst, under a condition that an organic solvent to be used for the reaction is a mixed solvent of acetic acid and a solvent selected from the group consisting of toluene, xylene and chlorobenzene, and a mixing ratio of acetic acid to the other solvent is from 1:3 to 1:5 in volume, wherein the reaction is conducted under heating and refluxing.

In the production method of the present invention, the organic solvent to be used is a mixed solvent of acetic acid and a solvent selected from the group consisting of toluene, xylene and chlorobenzene, and preferably, the mixing ratio of acetic acid to the other solvent is from 1:3 to 1:5 in volume, more preferably, from 1:4 to 1:5 in volume.

In the production method of the present invention, more preferably, the organic solvent to be used is a mixed solvent of acetic acid and toluene, and the mixing ratio of acetic acid to toluene is preferably from 1:3 to 1:5 in volume, more preferably, from 1:4 to 1:5 in volume. By conducting the reaction within the above described conditional range, not only that the reaction proceeds rapidly, but also that the dehydro-condensation product synthesized as a mixture of geometric isomers allows only the desired Z form having a poorer solubility to the mixed solvent to precipitate. This allows to suppress degradation by heating, and to enhance isomerization to the thermodynamically more stable Z form in a part of solution.

In the production method of the present invention, a compound expressed by formula (2) is preferably acetamide, benzamide, methyl carbamate, ethyl carbamate or benzyl carbamate, and more preferably, methyl carbamate or ethyl carbamate.

In the compound expressed by formula (3), a compound in which $R^2$ is methyl group is disclosed as the most preferable compound in conventional production methods. Since, however, compounds in which $R^2$ is methoxy or ethoxy group, have a higher stability than the compound in which $R^2$ is methyl group under the condition of the dehydro-condensation reaction, degradation of the product (which is the compound expressed by formula (3)) can be suppressed.

N-substituted-2-amino-4-(hydroxymethylphosphinyl)-2-butenoic acid derivative which is a production intermediate of herbicide, L-AMPB, can be produced by the production method of the present invention. Further, the production method of the present invention is advantageous in that the synthetic ratio of Z form increases in comparison with that in conventional production methods, resulting an improved yield, since the dehydro-condensation proceeds while being isomerized to a desired geometric isomer. Thus, the present invention is especially useful as a method for producing (Z)— N-substituted-2-amino-4-(hydroxymethylphosphinyl)-2-butenoic acid derivative.

Groups represented by $R^1$ and $R^2$ in the compounds expressed by formula (1) to (3), are described.

$C_{1-4}$ alkyl group represented by $R^1$ refers to straight or branched alkyl group having 1 to 4 carbons; more specifically, it is exemplified by methyl group, ethyl group, n-propyl group, isopropyl group, n-butyl group, 2-butyl group, isobutyl group, t-butyl group or the like, preferably, methyl group or ethyl group.

$C_{1-4}$ alkyl group represented by $R^2$ refers to straight or branched alkyl group having 1 to 4 carbons; more specifically, it is exemplified by methyl group, ethyl group, n-propyl group, isopropyl group, n-butyl group, 2-butyl group, isobutyl group, t-butyl group or the like, preferably, methyl group or ethyl group.

$C_{1-4}$ alkoxy group represented by $R^2$ refers to straight or branched alkoxy group having 1 to 4 carbons; more specifically, it is exemplified by methoxy group, ethoxy group, n-propoxy group, isopropoxy group, n-butoxy group, 2-butoxy group, isobutoxy group, t-butoxy group or the like, preferably, methoxy group or ethoxy group.

A group represented by $R^2$ or aryl group existing on the group is exemplified by phenyl group, naphthyl group or the like.

A substituted aryl group represented by $R^2$ denotes that 1 or more hydrogen atom(s), preferably, 1 to 3 hydrogen atom(s) on the benzene ring is(are) substituted, and the specific substitute(s) is(are) exemplified by straight or branched $C_{1-4}$ alkyl groups such as methyl group, ethyl group, n-propyl group, isopropyl group, n-butyl group, 2-butyl group, isobutyl group or t-butyl group etc.; halogen atoms such as fluorine, chlorine atom or bromine atom etc.; and $C_{1-4}$ alkoxy groups such as methoxy group etc.

A substituted aryloxy group represented by $R^2$ denotes that 1 or more hydrogen atom(s), preferably, 1 to 3 hydrogen atom(s) on the benzene ring is(are) substituted, and the specific substitute(s) is(are) exemplified by straight or branched $C_{1-4}$ alkyl groups such as methyl group, ethyl group, n-propyl group, isopropyl group, n-butyl group, 2-butyl group, isobutyl group or t-butyl group etc.; halogen atoms such as fluorine, chlorine atom or bromine atom etc.; and $C_{1-4}$ alkoxy groups such as methoxy group etc.

In the compound expressed by formula (1), it is preferable that $R^1$ is a hydrogen atom or $C_{1-4}$ alkyl group, more preferably a hydrogen atom.

As specific examples of the compounds expressed by formula (1), the following are exemplified:
2-oxo-4-(hydroxymethylphosphinyl)-butanoic acid,
2-oxo-4-(hydroxymethylphosphinyl)-butanoic acid methyl ester,
2-oxo-4-(hydroxymethylphosphinyl)-butanoic acid ethyl ester;
preferably, 2-oxo-4-(hydroxymethylphosphinyl)-butanoic acid.

In the compound expressed by formula (2), it is preferable that $R^2$ is $C_{1-4}$ alkyl group or $C_{1-4}$ alkoxy group, more preferably $C_{1-4}$ alkoxy group.

As specific examples of the compounds expressed by formula (2), the following are exemplified:
acetamide,
benzamide,
methyl carbamate,
ethyl carbamate,
benzyl carbamate;
preferably, methyl carbamate or ethyl carbamate.

In the compound expressed by formula (3), it is preferable that $R^1$ is a hydrogen atom or $C_{1-4}$ alkyl group, more preferably a hydrogen atom. It is preferable that $R^2$ is $C_{1-4}$ alkyl group or $C_{1-4}$ alkoxy group, more preferably $C_{1-4}$ alkoxy group.

As specific examples of the compounds expressed by formula (3), the following are exemplified:
(Z)-2-acetamide-4-(hydroxymethylphosphinyl)-2-butenoic acid,
(Z)-2-acetamide-4-(hydroxymethylphosphinyl)-2-butenoic acid methyl ester,
(Z)-2-acetamide-4-(hydroxymethylphosphinyl)-2-butenoic acid ethyl ester,
(Z)-2-propionylamino-4-(hydroxymethylphosphinyl)-2-butenoic acid,
(Z)-2-propionylamino-4-(hydroxymethylphosphinyl)-2-butenoic acid methyl ester,
(Z)-2-propionylamino-4-(hydroxymethylphosphinyl)-2-butenoic acid ethyl ester,
(Z)-2-methoxycarbonylamino-4-(hydroxymethylphosphinyl)-2-butenoic acid,
(Z)-2-methoxycarbonylamino-4-(hydroxymethylphosphinyl)-2-butenoic acid methyl ester, (Z)-2-methoxycarbonylamino-4-(hydroxymethylphosphinyl)-2-butenoic acid ethyl ester,
(Z)-2-ethoxycarbonylamino-4-(hydroxymethylphosphinyl)-2-butenoic acid,
(Z)-2-ethoxycarbonylamino-4-(hydroxymethylphosphinyl)-2-butenoic acid methyl ester,
(Z)-2-ethoxycarbonylamino-4-(hydroxymethylphosphinyl)-2-butenoic acid ethyl ester,
(Z)-2-benzoylamino-4-(hydroxymethylphosphinyl)-2-butenoic acid,
(Z)-2-benzoylamino-4-(hydroxymethylphosphinyl)-2-butenoic acid methyl ester,
(Z)-2-benzoylamino-4-(hydroxymethylphosphinyl)-2-butenoic acid ethyl ester,
(Z)-2-benzyloxycarbonylamino-4-(hydroxymethylphosphinyl)-2-butenoic acid,
(Z)-2-benzyloxycarbonylamino-4-(hydroxymethylphosphinyl)-2-butenoic acid methyl ester, or
(Z)-2-benzyloxycarbonylamino-4-(hydroxymethylphosphinyl)-2-butenoic acid ethyl ester; preferably
(Z)-2-methoxycarbonylamino-4-(hydroxymethylphosphinyl)-2-butenoic acid or (Z)-2-ethoxycarbonylamino-4-(hydroxymethylphosphinyl)-2-butenoic acid.

In the production method of the present invention, the organic solvent to be used is preferably a mixed solvent of acetic acid and a solvent selected from the group consisting of toluene, xylene and chlorobenzene. More preferably, the organic solvent is the mixed solvent of acetic acid and toluene. The mixing ratio of acetic acid to the other solvent is preferably from 1:3 to 1:5 in volume, more preferably, from 1:4 to 1:5 in volume. By conducting the reaction within the above described conditional range, not only that the reaction proceeds rapidly, but also that the dehydro-condensation product synthesized as a mixture of geometric isomers allows only the desired Z form having a poorer solubility to the mixed solvent to precipitate. This allows to suppress degradation by heating, and to enhance isomerization to the thermodynamically more stable Z form in a part of solution.

In the production method of the present invention, the amount to be used of the mixed solvent is preferably from 5 to 20 folds volume based on the weight of the compound expressed by formula (1), more preferably, from 7 to 10 folds volume.

For example, as described in J. Org. Chem. 1987, 52, 5143-5130, it has been known that the geometric isomer mixture of dehydroamino acid derivative which results from the reaction of dehydro-condensation can be isomerized to Z form by using an acid catalyst. In the production method of the present invention, the mixture of the geometric isomers of N-substituted-2-amino-4-(hydroxymethylphosphinyl)-2-butenoic acid derivative can also be isomerized to the desired Z form. While an acid catalyst can be used as needed, mineral acids such as hydrochloric acid, sulfuric acid; or organic acids such as methanesulfonic acid, benzenesulfonic acid, p-toluenesulfonic acid, trifluoroacetic acid are exemplified as a usable acid catalyst, preferably hydrochloric acid, p-toluenesulfonic acid. The amount to be used of the acid catalyst is preferably, within an amount of from 0.01 to 0.5 equivalents based on the amount of the compound expressed by formula (1), more preferably, from 0.02 to 0.1 equivalents. The process of isomerization may be conducted together with the proceeding of the reaction of dehydro-condensation, while it may be conducted separately after the completion of the reaction of dehydro-condensation.

In the production method of the present invention, as a compound expressed by formula (2), the following are exemplified: acetamide, benzamide, methyl carbamate, ethyl carbamate or benzyl carbamate; more preferably methyl carbamate or ethyl carbamate. The amount to be used of the compound expressed by formula (2) is preferably, within an amount of from 1 to 5 equivalents based on the amount of the compound expressed by formula (1), more preferably, from 1.1 to 2.0 equivalents.

In the production method of the present invention, while a reaction temperature differs depending on a solvent to be used, it is within a range of from 20 to 150 deg. C., preferably, from 80 to 120 deg. C. The reaction is usually conducted with separating water generated, preferably conducted by using separators such as Dean-Stark trap or the like. The reaction is usually conducted for a period of reaction time in a range of from 1 to 10 hours, preferably from 3 to 7 hours.

Since the compound expressed by formula (3) is precipitated in a reaction solution, it can be isolated by filtrating the reaction solution or the precipitation obtained by replacing a solvent which is concentrated under a reduced pressure, with another applicable solvent can be isolated by filtration.

EXAMPLES

Hereinafter, the present invention is specifically described by way of examples, but is not limited to these examples. The area ratios of Z form and E form described in Examples are determined by HPLC under the following condition.
Column: Develosil 5C30-U-G 4.6×250 mm (Nomura Chemical Co., Ltd)
Column temperature: a constant temperature close to room temperature
Mobile phase: A=0.1% phosphoric acid aqueous solution, B=acetonitrile

TABLE 1

|   | 0 min. | 15 min. | 15.01-20 min. | 20.01-30 min. |
|---|---|---|---|---|
| A | 100 | 30 | 50 | 100 |
| B | 0 | 70 | 50 | 0 |

Flow rate: 1.0 mL/m
Detection: UV 210 nm

Example 1

(Z)-2-methoxycarbonylamino-4-(hydroxymethylphosphinyl)-2-butenoic acid 7.085 g of methyl carbamate, 0.275 g of p-toluenesulfonic acid monohydrate and 10.000 g of 2-oxo-4-(hydroxymethylphosphinyl)-butanoic acid prepared by the method described in Japanese Patent Laid-Open No. 92897/1981, were added to 16 mL of acetic acid to be suspended. After being dissolved by heating, 64 mL of toluene was added thereto and then the solution was refluxed with vigorous stirring. The internal temperature of the reaction solution was from 106 to 108 deg. C. One and a half hours later, 8 mL of toluene was further added to the reaction solution and continued stirring. Three hours later, dissipation of almost all the raw materials was confirmed by HPLC measurement. At this point, the area ratio of Z form to E form was 94:6. After removing about 60 mL of the solvent under a reduced pressure, followed by adding 20 mL of acetic acid, and then the resultant was stirred for 1 hour at 80 deg. C. The precipitate which was obtained by cooling the solution gradually to room temperature and stirring over-night, was filtered and then the filtrate was washed with acetic acid. After being washed with acetone, dried for 5 hours from 40 to 50 deg. C. under a reduced pressure, 10.625 g of the objective compound was obtained (80.7% yield, Z:E=99.6:0.4).

mp 254-256 deg. C.

1H-NMR (D20) [delta] 6.59 (dt, 1H, J=6.8, 8.1 Hz), 3.55 (s, 3H), 2.68 (dd, 2H, J=8.3, 18.8 Hz), 1.31 (d, 3H, J=14.2 Hz)

MS (ES+) m/z 238 [M+H]+

Example 2

(Z)-2-acetamide-4-(hydroxymethylphosphinyl)-2-butenoic acid 6.559 g of acetamide, 0.275 g of p-toluenesulfonic acid monohydrate and 10.000 g of 2-oxo-4-(hydroxymethylphosphinyl)-butanoic acid were added to 16 mL of acetic acid to be suspended. After being dissolved by heating, 72 mL of toluene was added thereto and then the solution was refluxed with vigorous stirring. The internal temperature of the reaction solution was from 106 to 108 deg. C. Three hours later, dissipation of almost all the raw materials was confirmed by HPLC measurement. At this point, the area ratio of Z form to E form was 92:8. After removing about 60 mL of the solvent under a reduced pressure, followed by adding 20 mL of acetic acid and then the resultant was stirred for 30 minutes at 80 deg. C. The precipitate which was obtained by cooling the solution gradually to room temperature and stirring over-night, was filtered and then the filtrate was washed with acetic acid. After being washed with acetone, dried for 5 hours from 40 to 50 deg. C. under a reduced pressure, 8.138 g of the objective compound was obtained (66.3% yield, Z:E=99.8:0.2).

The spectral data of the compound obtained corresponds to that described in J. Org. Chem., 56, 1783-1788 (1991).

Example 3

(Z)-2-methoxycarbonylamino-4-(hydroxymethylphosphinyl)-2-butenoic acid 5.835 g of methyl carbamate and 10.000 g of 2-oxo-4-(hydroxymethylphosphinyl)-butanoic acid were added to 17 mL of acetic acid to be suspended. After being dissolved by heating, 68 mL of toluene was added thereto and then the solution was refluxed with vigorous stirring. The internal temperature of the reaction solution was from 106 to 108 deg. C. Four hours later, dissipation of almost all the raw materials was confirmed by HPLC measurement. At this point, the area ratio of Z form to E form was 94:6. After removing about 42 mL of the solvent under a reduced pressure, followed by adding 23 mL of acetic acid, and then the resultant was stirred for 1 hour at 80 deg. C. The precipitate which was obtained by cooling the solution gradually to room temperature and stirring over-night, was filtered and then the filtrate was washed with acetic acid. After being washed with acetone, dried for 5 hours from 40 to 50 deg. C. under a reduced pressure, 9.931 g of the objective compound was obtained (75.4% yield, Z:E=99.6:0.4).

Example 4

(Z)-2-methoxycarbonylamino-4-(hydroxymethylphosphinyl)-2-butenoic acid 5.835 g of methyl carbamate, 0.275 g of p-toluenesulfonic acid monohydrate and 10.000 g of 2-oxo-4-(hydroxymethylphosphinyl)-butanoic acid were added to 16 mL of acetic acid to be suspended. After being dissolved by heating, 80 mL of chlorobenzene was added thereto and then the solution was refluxed with vigorous stirring. A remaining solution was removed appropriately while the internal temperature of the reaction solution was maintained from 106 to 110 deg. C. under a slightly reduced pressure, followed by adding chlorobenzene, the volume of which was equal to the volume of the removed solution. Two hours later, dissipation of almost all the raw materials was confirmed by HPLC measurement. At this point, the area ratio of Z form to E form was 93:7. After removing about 50 mL of the solvent under a reduced pressure, followed by adding 20 mL of acetic acid, and then the resultant was stirred for 1 hour at 80 deg. C. The precipitate which was obtained by cooling the solution gradually to room temperature and stirring over-night, was filtered and then the filtrate was washed with acetic acid. After being washed with acetone, dried for 6 hours from 40 to 50 deg. C. under a reduced pressure, 9.505 g of the objective compound was obtained (72.2% yield, Z:E=99.5:0.5).

Example 5

(Z)-2-methoxycarbonylamino-4-(hydroxymethylphosphinyl)-2-butenoic acid 67.56 g of methyl carbamate, 2.97 g of p-toluenesulfonic acid monohydrate and 108.06 g of 2-oxo-4-(hydroxymethylphosphinyl)-butanoic acid were added to 160 mL of acetic acid to be suspended. After being dissolved by heating, 800 mL of toluene was added thereto and then the solution was refluxed with vigorous stirring. According to the same procedure as Example 1, 102.28 g of the objective compound was obtained (71.9% yield, Z:E=99.8:0.2).

Comparative Example 1

(Z)-2-methoxycarbonylamino-4-(hydroxymethylphosphinyl)-2-butenoic acid 16.673 g of methyl carbamate, 0.549 g of p-toluenesulfonic acid monohydrate, and 20.000 g of 2-oxo-4-(hydroxymethylphosphinyl)-butanoic acid were added to 56 mL of acetic acid to be suspended. After being dissolved by heating, 112 mL of toluene was added thereto and then the solution was refluxed with vigorous stirring. The internal temperature of the reaction solution was from 106 to 108 deg. C. Six hours later, dissipation of almost all the raw materials was confirmed by HPLC measurement. At this point, the area ratio of Z form to E form was 81:19. The deposited precipitate was filtered and then the filtrate was washed with acetic acid. After being washed with acetone, dried for 5 hours from 40 to 50 deg. C. under a reduced pressure, 14.966 g of the objective compound was obtained (56.8% yield, Z:E=99.7:0.3).

The particular exemplary embodiments or examples may be modified or adjusted within the scope of the entire disclosure of the present invention, inclusive of claims, based on the fundamental technical concept of the invention. In addition, a variety of combinations or selections of elements disclosed herein may be made within the context of the claims. That is, the present invention may cover a wide variety of modifications or corrections that may occur to those skilled in the art in accordance with the entire disclosure of the present invention, inclusive of claims, and the technical concept of the present invention.

In addition, it should be understood that the effect of claiming the priority in the present application is based on the provision of the Paris Convention, the effect should be considered solely on the basis of the Description of the earlier application (Japanese patent application No. 2010-136373) based on which the priority is claimed.

The invention claimed is:

1. A method for producing a compound expressed by the following formula (3):

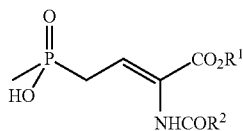

(3)

[where $R^1$ represents a hydrogen atom or $C_{1-4}$ alkyl group, and $R^2$ represents $C_{1-4}$ alkyl group, $C_{1-4}$ alkoxy group, aryl group, aryloxy group or benzyloxy group], the method comprising a reaction of dehydro-condensing a compound expressed by the following formula (1):

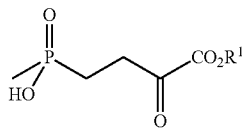

(1)

[where $R^1$ represents the same meaning as defined above], and a compound expressed by the following formula (2):

$$H_2N\text{---}COR^2 \qquad (2)$$

[where $R^2$ represents the same meaning as defined above], while being converted to a desired geometric isomer in the presence or absence of an acid catalyst, under a condition that an organic solvent to be used for the reaction is a mixed solvent of acetic acid and a solvent selected from the group consisting of toluene, xylene and chlorobenzene, and a mixing ratio of acetic acid to the other solvent is from 1:3 to 1:5 in volume, wherein the reaction is conducted under heating and refluxing.

2. The method as defined in claim 1, wherein the organic solvent to be used for the reaction is a mixed solvent of acetic acid and toluene.

3. The method as defined in claim 1, wherein the organic solvent to be used for the reaction is a mixed solvent of acetic acid and toluene, and wherein the mixing ratio of acetic acid to toluene is from 1:4 to 1:5 in volume.

4. The method as defined in claim 1, wherein $R^2$ is methoxy group or ethoxy group.

5. The compound expressed by formula (3) defined in claim 1, wherein the compound is (Z)-2-methoxycarbonylamino-4-(hydroxymethylphosphinyl)-2-butenoic acid.

6. The method as defined in claim 2, wherein $R^2$ is methoxy group or ethoxy group.

7. The method as defined in claim 3, wherein $R^2$ is methoxy group or ethoxy group.

* * * * *